(12) United States Patent
Nigam

(10) Patent No.: US 7,992,906 B2
(45) Date of Patent: *Aug. 9, 2011

(54) SYSTEM FOR PACKAGING AND HANDLING AN IMPLANT AND METHOD OF USE

(75) Inventor: Alok Nigam, Trabuco Canyon, CA (US)

(73) Assignee: ReVision Optics, Inc., Lake Forest, CA (US)

( * ) Notice: Subject to any disclaimer, the term of this patent is extended or adjusted under 35 U.S.C. 154(b) by 1046 days.

This patent is subject to a terminal disclaimer.

(21) Appl. No.: 11/422,815

(22) Filed: Jun. 7, 2006

(65) Prior Publication Data

US 2006/0212041 A1    Sep. 21, 2006

Related U.S. Application Data

(60) Continuation of application No. 11/054,639, filed on Feb. 9, 2005, now Pat. No. 7,128,351, which is a continuation of application No. 10/463,091, filed on Jun. 17, 2003, now Pat. No. 6,893,461, which is a division of application No. 09/843,547, filed on Apr. 26, 2001, now Pat. No. 6,581,993, which is a continuation-in-part of application No. 09/660,371, filed on Sep. 12, 2000, now Pat. No. 6,543,610.

(51) Int. Cl.
*A61F 9/00* (2006.01)

(52) U.S. Cl. ............... 294/1.2; 206/5.1; 606/107

(58) Field of Classification Search ............ 294/1.2; 206/5.1; 606/107; 623/5.11, 6.12

See application file for complete search history.

(56) References Cited

U.S. PATENT DOCUMENTS

| | | | | |
|---|---|---|---|---|
| 3,168,100 A * | 2/1965 | Rich | ............... | 134/137 |
| 3,343,657 A * | 9/1967 | Speshyock | ............... | 206/5 |
| 3,379,200 A * | 4/1968 | Pennell | ............... | 134/143 |
| 3,770,113 A * | 11/1973 | Thomas | ............... | 206/5 |
| 4,039,827 A * | 8/1977 | Zdrok et al. | ............... | 250/271 |
| 4,071,272 A * | 1/1978 | Drdlik | ............... | 294/1.2 |
| 4,257,521 A * | 3/1981 | Poler | ............... | 206/5.1 |
| 4,423,809 A * | 1/1984 | Mazzocco | ............... | 206/5.1 |
| 4,490,860 A * | 1/1985 | Rainin | ............... | 623/6.11 |
| 4,545,478 A * | 10/1985 | Waldman | ............... | 206/5.1 |
| 5,941,583 A * | 8/1999 | Raimondi | ............... | 294/1.2 |
| 6,543,610 B1 * | 4/2003 | Nigam | ............... | 206/5.1 |
| 6,581,993 B2 * | 6/2003 | Nigam | ............... | 294/1.2 |
| 6,824,178 B2 * | 11/2004 | Nigam | ............... | 294/1.2 |
| 7,128,351 B2 * | 10/2006 | Nigam | ............... | 294/1.2 |

* cited by examiner

*Primary Examiner* — Dean J Kramer
(74) *Attorney, Agent, or Firm* — Shay Glenn LLP

(57) ABSTRACT

A system designed to store an implant together with the tools necessary to implant the stored implant, and a method of using such system. Such system includes an implant storage tool adapted to retain the implant within a storage container. The implant storage tool is operable to provide an implant applicator.

17 Claims, 17 Drawing Sheets

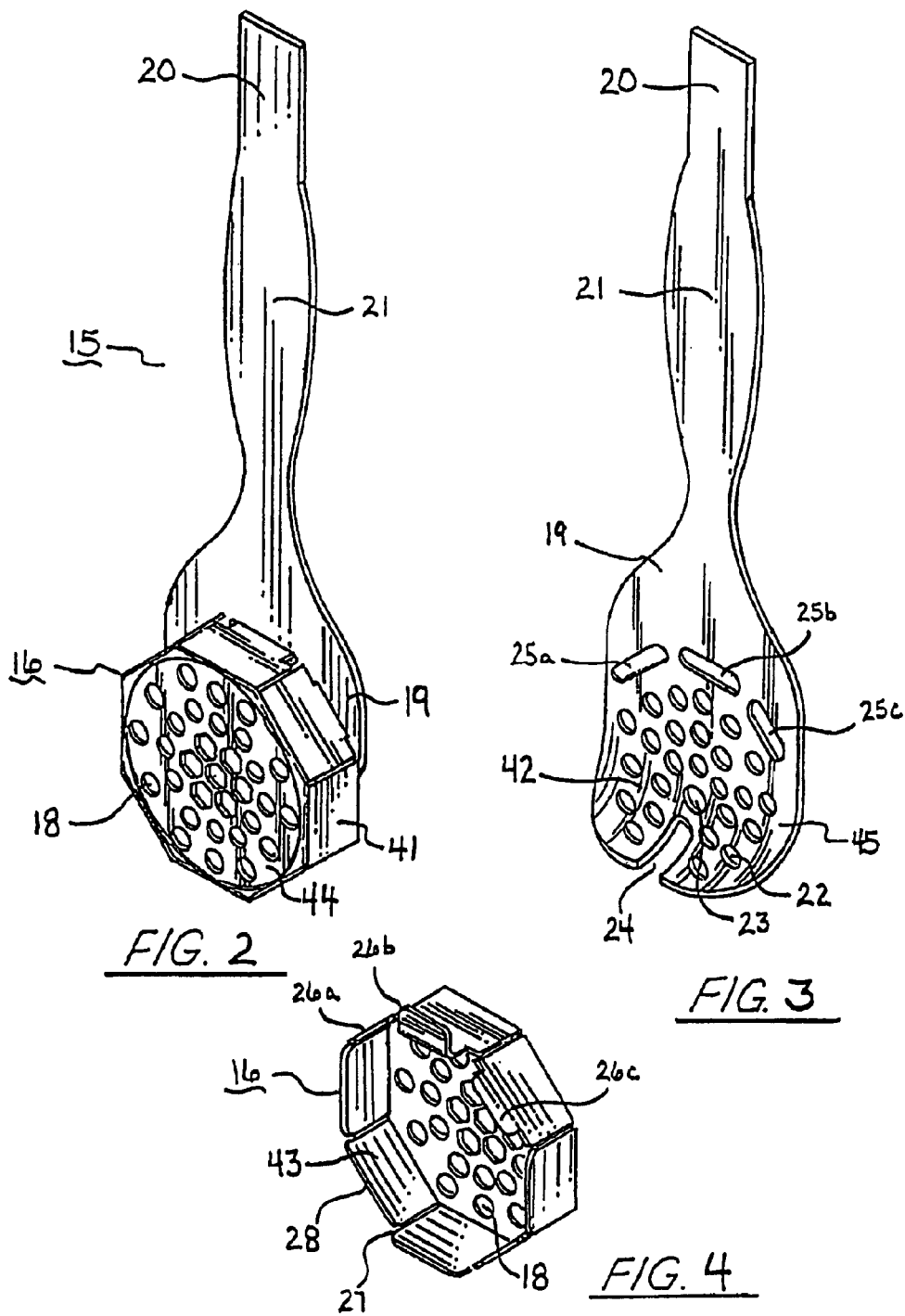

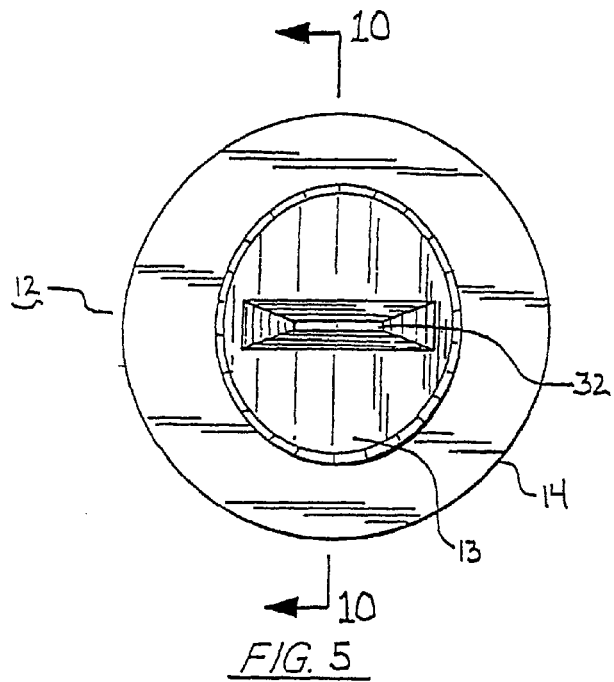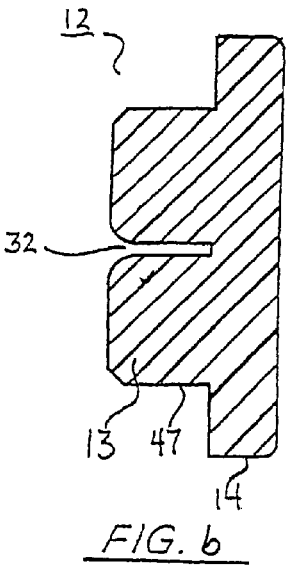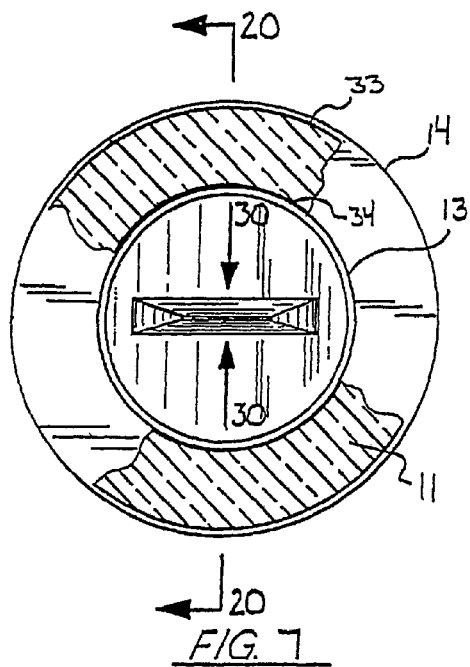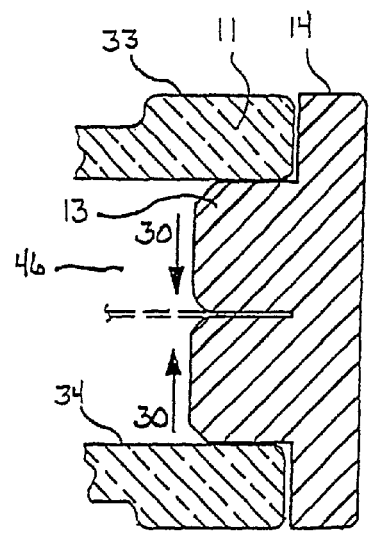
FIG. 5
FIG. 6
FIG. 7
FIG. 8

SYSTEM FOR PACKAGING AND HANDLING AN IMPLANT AND METHOD OF USE

This application is a continuation of application Ser. No. 11/054,639 filed on Feb. 9, 2005, now U.S. Pat. No. 7,128,351 which is a continuation of U.S. application Ser. No. 10/463,091, filed on Jun. 17, 2003, now U.S. Pat. No. 6,893,461, which is a divisional of my presently U.S. application Ser. No. 09/843,547, filed on Apr. 26, 2001, now U.S. Pat. No. 6,581,993, which is a continuation-in-part of U.S. application Ser. No. 09/660,371, filed on Sep. 12, 2000, now U.S. Pat. No. 6,543,610.

FIELD OF THE INVENTION

The present invention relates to a system for packaging, handling and applying implants. Additionally, this invention relates to a method for introducing a corneal implant to the corneal surface.

BACKGROUND OF THE INVENTION

Current methods and devices used to store small, delicate, and normally transparent implants entail free-floating the implant in a volume of storage fluid contained within a storage bottle or other container. This manner of storage is oftentimes used to preserve retinal transplants, brain tissue transplants, corneal implants, tissue biopsies and any other delicate biological specimen. Free-floating storage, however, subjects a stored specimen or implant to fluid agitation, which can severely and irreparably damage the integrity of the stored material. In addition, isolating transparent specimens from the storage fluid is difficult to achieve.

Corneal implants are especially susceptible to the above described problem. Corneal implants are used to correct visual disorders such as Myopia or near-sightedness, Hyperopia or farsightedness, Presbyopia or difficulty in accommodating a change in focus, and Astigmatism. To correct these disorders, the implant is introduced into the body of the cornea in known ways, such as after a flap is formed and an under surface of the cornea is exposed. The implant, changes the shape of the cornea and alters its refractive power. These implants are generally made of various types of hydrogels, but can include other polymers, tissue implants, or the like. In the past, storing the corneal implant required free-floating the implant in a volume of storage fluid contained within a storage container. To retrieve the implant, one had to first locate the implant within the fluid, and then remove the implant using a filter device or sequestering tool. In the case of a corneal implant, locating the implant is complicated by both the size and transparency of the implant. For instance, a corneal implant generally has a diameter of about 4.0 to 7.0 mm and a center that is normally fabricated having a thickness ranging from 25 to 50 microns. Due this minuscule size, physically grasping the implant from the storage fluid using tweezers, or the like, is simply not practical.

Successful isolation of a corneal implant, or other specimen, generally requires the use of a sieve to separate the implant from the fluid. Isolating the implant in this manner, however, subjects the implant to mechanical forces, which could lead to a loss of the implant. If not damaged, the transparent implant must still be located-on the sieve surface and retrieved. The implant must therefore be grasped using tweezers, forceps, or the like. Imparting such force upon the implant, however, can also damage the implant. Using force imparting tools to hold the implant is therefore not desirable. Current isolation techniques are therefore difficult, time-consuming and create additional steps, which can also lead to implant contamination. Thus, it is desired to have an implant storage and handling system, which allows the user to rapidly and successfully retrieve the implant for prompt implantation.

Current devices used to deposit an implant onto the cornea surface generally deposit the corneal implant onto the cornea surface in a bunched or folded conformation. Aligning the implant in planar relation to the cornea surface requires the surgeon to manipulate or tease the implant so as to remove any folds or bends in the implant. Problematically, the step of unfolding the implant on the cornea surface can cause serious trauma to the cornea surface. This trauma can lead to the formation of edema, or other deleterious responses that lead to rejection or displacement of the implant.

Thus, there is believed to be a demonstrated need for a unitary packaging and handling system that provides the desired storage capabilities, easy retrieval of the specimen from that storage, and tools that are operable to retrieve and utilize the specimen without causing damage to the specimen or an implantation site. There is also an additional need for a more effective method for implanting a corneal implant onto a cornea surface.

SUMMARY OF THE INVENTION

The present invention relates to an implant packaging and handling system which includes a storage bottle having an opening to receive a volume of implant storage fluid, and an implant holding tool designed to retain the implant in fluid communication with the implant storage fluid. A storage bottle stopper holds the implant holding tool, so that a portion of the implant holding tool is immersed within the storage fluid upon placement of the stopper into the bottle, placing the implant in fluid communication with the storage fluid. The implant holding tool includes a retaining member detachably mounted to an implant applicator tool. Together they define an enclosure for retaining the implant in a secure, known storage position.

The implant applicator tool has an arcuate-shaped applicator surface with a plurality of openings. The arcuate shaped surface is contoured to correspond to the curvature of the cornea surface, which aids in the proper implantation of the implant to the cornea surface. In one embodiment, the applicator surface has one or more recessed surfaces designed to hold and center the implant on the applicator surface. One or more recessed grooves are also provided to allow fluid to flow between the implant and the applicator surface.

The openings have numerous advantages. The openings provide continuous fluid communication between a retained implant and the implant storage fluid. Upon removal from storage, the openings enable the user to unfold and orient the implant by gently passing fluid through the openings so as to float the implant into a desired central position on the applicator tool surface. Once so positioned, the user is then able to aspirate the fluid/from between the implant and the applicator tool, the applicator tool surface. The applicator tool also includes a central opening providing the user with a reference point for centering the applicator surface, and thus, the implant onto the surface of the cornea.

The present invention also relates to a method of implanting a corneal implant using the implant packaging and handling system. The initial step includes surgically preparing the cornea surface for implantation. Next, the implant and implant holding tool are retrieved from the storage bottle, and the retaining member removed so as to provide an applicator tool together with implant. The applicator can then be attached to a handle for ease of use. The implant is then properly aligned on the applicator tool and deposited onto the surgically prepared cornea surface. Finally, the cornea is restored.

BRIEF DESCRIPTION OF THE DRAWINGS

A better understanding of the invention can be obtained from the detailed description of exemplary embodiments set forth below, when considered in conjunction with the appended drawings, in which:

FIG. 2 is a schematic representation of the implant applicator tool fastened to a retaining member, providing the implant storage tool of the present invention;

FIG. 3 is a schematic representation of the implant applicator tool of the present invention;

FIG. 4 is a schematic representation of the retaining member adapted to form an implant retaining enclosure when fastened to the implant applicator tool of FIG. 3;

FIG. 5 is a bottom view of a stopper used to seal the storage bottle of the present invention, showing the implant storage tool engagement slot in an open position;

FIG. 6 is a cross-sectional view through the stopper of FIG. 5 taken on line 10-10;

FIG. 7 is a partial sectional view of the bottle stopper positioned within the storage bottle, showing the implant storage tool engagement slot in a closed position;

FIG. 8 is a cross-section at view through the stopper and storage bottle of FIG. 7 taken on line 20-20;

FIG. 16c is a cross-sectional view across line B-B of the upper lens carrier member shown in FIG. 16a.

DETAILED DESCRIPTION OF EXEMPLARY EMBODIMENTS

Figure 1:
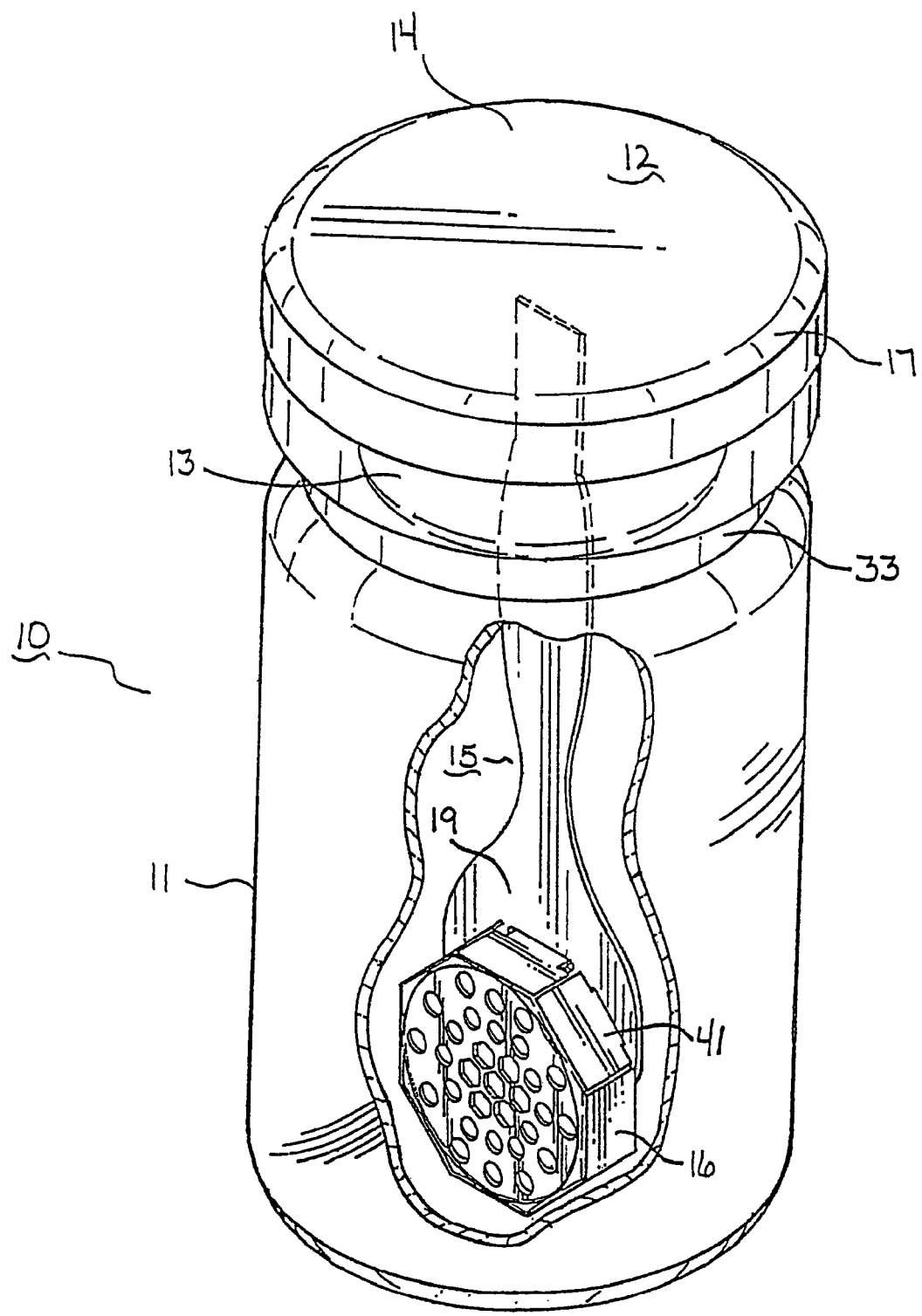
FIG. 1 is a partial sectional view of the implant packaging and handling system of the present invention.

FIGS. 1 through 17b of the drawings show an implant packaging and handling system 10 of the present invention. As illustrated in FIG. 1, the preferred system 10 includes a cylindrical storage bottle 11 for holding implant storage fluid (not indicated). The bottle 11 is sealed by a stopper 12 having an upper cap portion 14 and a plug portion 13, which is adapted to detachably couple to an implant storage tool 15. A protective safety seal 17 provides tamper resistance and maintains the stopper 12 in sealed relation to the bottle 11.

FIGS. 2 through 4 show a retaining member 16 and implant applicator tool 19, which together define the implant storage tool 15. As illustrated, the retaining member 16 is adapted to detachably engage the implant applicator tool 19, thereby defining an enclosure 41 operable to retain the implant. Both the retaining member 16 and the applicator tool 19 include a plurality of openings 18 and 22, respectively, which allow storage fluid to communicate into the implant retaining enclosure 41. As shown in FIG. 1, the implant retaining enclosure 41 is located on the end of storage tool 15 that is distal to the stopper 12 such that the enclosure 41 is immersed in implant storage fluid when the storage tool 15 is inserted into the bottle 11. When the implant is stored, the enclosure 41 of storage tool 15 holds the implant in the storage fluid, while also providing a user with ready access to the implant. The user simply removes the stopper 12, thereby removing the storage tool 15 from the bottle 11, and detaches the retaining member 16 from the applicator 19 to access the implant.

As illustrated in FIG. 3, applicator tool 19 has a handle attachment arm 20 connected through a body portion 21 to an implant applicator member 45. The body portion 21 is preferably shaped to provide a broad handling surface. For instance, FIGS. 2 and 3 show a body portion 21 having a broad elliptical shape, which allows a user to more easily manipulate the applicator tool 19. As shown, the implant applicator member 45 includes an applicator surface 42 having a plurality of openings 22 to provide fluid communication between the applicator surface 42 and an implant resting thereon. Openings 22 further allow the user to release the implant from the applicator surface 42. More particularly, the user can impart force upon the implant by passing through the opening 22 either a flow of fluid or a cantilever so as to forcibly separate the implant from the applicator member surface 42 (as is shown in FIG. 14).

In a preferred embodiment, the applicator surface 42 has a central opening 23 to help the user align the applicator surface 42 along the visual or optical axis of the eye. As shown, the centrally positioned opening 23 defines a circular opening having a diameter greater than the diameter of the surrounding openings 22. In this way, the user is provided with a central point of reference, which enables the user to align the applicator surface 42 with the optical axis of the eye, and thus, properly position the implant.

Figure 12:
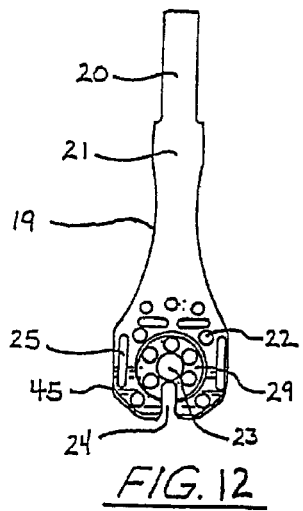
FIG. 12 is a schematic representation of an implant applicator tool having a recessed surface defining a central opening and adjacent alignment slot.

In another embodiment, the applicator tool 19 may include an applicator alignment notch 24 positioned integral to the surface 42 of the applicator member 45. For instance, FIGS. 3 and 12 show the notch 24 extending inwardly towards the centrally positioned alignment opening 23. In this embodiment, the notch 24 is used to align the implant on the cornea surface 39, as well as release the implant from the applicator surface 42. Specifically, the notch 24 is dimensioned to allow a cantilever, or like instrument, to pass through the notch, thereby allowing the user to impart force against an implant held on the applicator surface 42. Specifically, the user lifts the application tool 19 away from the cornea surface while simultaneously imparting downward force on the implant through the notch 24 so as to release the implant. One skilled in the art will understand that various notch positionings can be incorporated into the applicator member 45 without departing from the scope of the present invention.

As shown in FIG. 2, the retaining member 16 has an outer surface 44 defining a plurality of openings 18 that provide fluid communication to an implant retained by the enclosure 41. FIG. 4 shows a retaining member 16 disengaged from the applicator tool 19 shown in FIG. 3. To secure the retaining member 16 to the applicator tool 19, the retaining member 16 is provided with attachment tabs 26a-c adapted to insert into corresponding attachment slots 25a-c integral to the applicator tool 19. In use, the retaining member 16 is attached to the applicator tool 19 by simply inserting the tabs 26a-c into the respective corresponding slots 25a-c, and then positioning the bottom surfaces 28 of retaining member side walls 43 against the applicator surface 42. In a preferred embodiment, at least one side wall 43 has an overlapping flexible portion 27 adapted to bend about the distal edge of the applicator surface 42, thereby securely clamping the retaining member 16 to the applicator tool 19. To remove the retaining member 16, the user merely unclamps the flexible portion 27 by bending it away from the applicator tool 19, and lifting the member 16 so as to disengage tabs 26a-c from slots 25a-c.

As illustrated in FIGS. 9, 11, 12 and 13, an alternative attachment tab 26 and attachment slot 25 can also be used with the present invention. For instance, FIG. 12 shows an applicator tool 19 having four separate attachment slots 25, while in comparison FIG. 3 shows an applicator tool 19 having three separate attachment slots 25a-c. It will be understood by those skilled in the art that various embodiments for attachment slots 25 and tabs 26 can be incorporated into the applicator tool 19 and retaining member 16 without deviating from the scope of the present invention.

As illustrated in FIGS. 5 through 8, a preferred embodiment of system 10 includes a bottle stopper 12 adapted to receive and securely hold the handle attachment arm 20 of the applicator tool 19. The stopper 12 preferably includes an upper cap portion 14 and a plug portion 13 dimensioned to insertably seal the bottle 11. FIG. 5 shows the stopper plug portion 13, which is not inserted into a storage bottle opening 46 (shown in FIG. 8). In comparison to FIG. 5, FIG. 7 shows the plug 13 inserted into the storage bottle opening 46. As illustrated by FIGS. 5 and 7, plug portion 13, when removed from bottle opening 46, adopts an elliptical shape by distending in an outwardly direction along line the 10-10. Likewise, inserting stopper 12 into bottle opening 46 causes the outer diameter of plug portion 13 to conform to the inner diameter of the inner bottle surface 34. In this way, the plug portion 13 becomes inwardly compressed along line 30-30. Referring to FIGS. 6 and 8, cross-section views are shown of stopper plug portion 13 in an out-of-bottle elliptical shape and an in-bottle compressed circular shape, respectively. The utility of this embodiment is described in more detail below.

An engagement slot 32 is located integral to plug portion 13 in an orientation perpendicular to line 10-10. As illustrated in FIGS. 5 through 8, the engagement slot 32 opens or closes in response to either the removal or insertion of the plug portion 13 from the bottle opening 46, respectively. Referring to FIGS. 5 and 6, the engagement slot 32 is shown in an open position. More particularly, when the user removes the stopper 12 from bottle opening 46, the plug portion 13 adopts an unrestrained elliptical shape by distending outwardly along the line 10-10 for opening slot 32. In this way, the engagement arm 20 of the applicator tool 19, which is held by the engagement the slot 32, is easily separated from slot 32 once the stopper 12 is removed from the storage bottle 11. By way of comparison, FIGS. 7 and 8 show the engagement slot 32 adopting a closed conformation upon insertion of the stopper 12 into the bottle opening 46. As shown in FIG. 7, insertion of the stopper 12 into the bottle 11 causes the outer surface 47 of the plug portion 13 to conform to the inner diameter of the bottle opening surface 34, which imparts force in the direction of the line 30-30. In this way, the slot 32 is forced into a tight, closed conformation. Thus, the engagement arm 20 of the applicator tool 19 is held by a slot 32 in a secure position when the stopper 12 is inserted into the bottle 11. The stopper 12 is preferably made of silicone rubber, or other elastomeric material.

Figure 10:
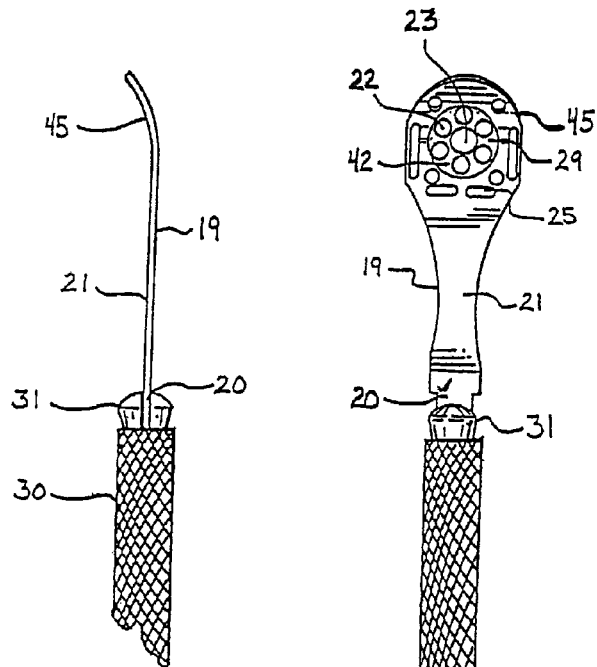
FIG. 10 is a side view of the implant applicator tool secured to a handle, showing the curved surface of the implant applicator tool, which corresponds with the contour of the cornea surface.
Figure 9:
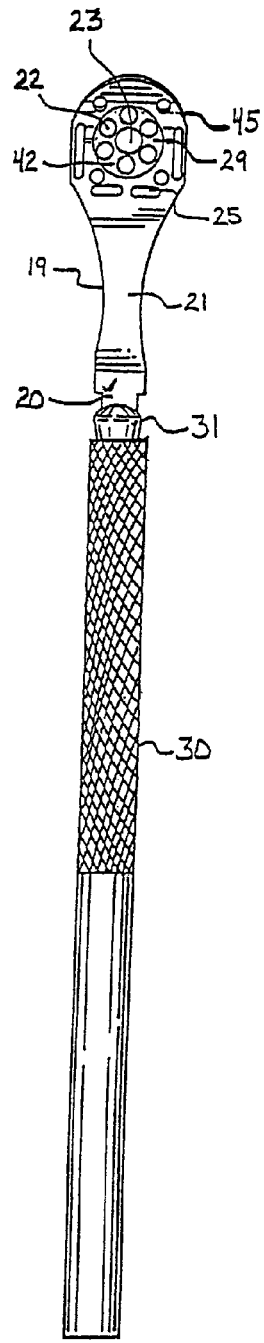
FIG. 9 is a schematic illustration of the implant applicator tool secured to a handle.

FIGS. 9 and 10 show an applicator tool 19 attached to a handle 30. The applicator tool attachment arm 20 detachably mounts to the handle 30 through a handle fastener 31. It will be understood by those skilled in the art that numerous types of handles and handle fasteners are available that can be used with the applicator tool 19 without departing from the scope of the present invention.

As illustrated by FIG. 10, the implant applicator member 45 has a curved applicator surface 42, which corresponds to the curvature of the cornea implant site. This curved surface allows the user to position the curved applicator surface 42 evenly across the cornea surface, enabling the implant to be more evenly deposited onto the cornea surface. Referring to FIGS. 9 and 12, each applicator member 45 is shown having a recessed applicator surface 29. As shown, the recessed surface 29 is preferably circular, thereby allowing a substantially circular implant to be centrally positioned on the applicator member 45. In addition, the central opening 23 which is centered relative to the perimeter of the circular recess 29, provides the user with a reference point for alignment of the applicator member 45 with the pupil diameter. In this way, the implant can be properly aligned on the cornea surface.

Figure 11:
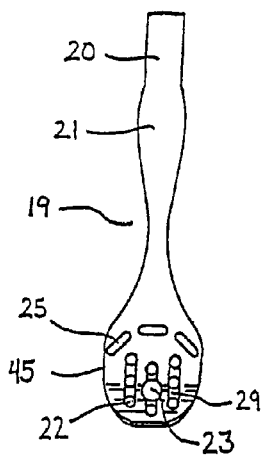
FIG. 11 is a schematic representation of an implant applicator tool having a central opening for aligning the applicator tool with the visual or pupillary axis of the eye.

FIG. 11 shows an applicator tool 19 having an applicator surface 42 with recessed grooves 29 to allow fluid to flow between the applicator surface 42 and an implant supported on the surface 42. It should be understood by one skilled in the art that alternatively dimensioned recesses and grooves can be formed in the applicator surface 42 without departing from the scope of the present invention. It is advantageous to provide fluid flow between the surface 42 and the implant to enable the user to more easily manipulate the implant while it is on the applicator surface 42. During storage, for example, the implant may come to rest in various folded and bunched conformations. Once the retaining member 16 is removed, the user can manipulate the implant into its desired conformation by gently passing a volume of fluid through the openings 22 and 23. More particularly, the implant will overlap a small volume of fluid, thereby allowing the user to floatingly realign the implant on the applicator surface 42. After the implant is aligned, the fluid can be removed by simply touching the underside of the applicator member 45 with a cotton swab, or like absorbent material.

Figure 13:
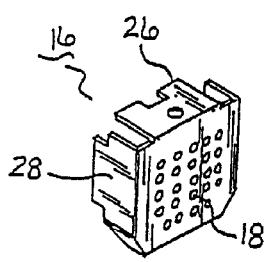
FIG. 13 is a schematic representation of a retaining member adapted to engage with the applicator tools shown in FIGS. 9 and 12.
Figure 13A:
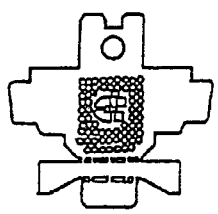
FIG. 13a shows the retaining member in a planar configuration, i.e., before tabs 26 and 28 have been folded down as shown in FIG. 13.

FIGS. 12 and 13 show an alternative embodiment of an applicator tool 19 and a retaining member 16, respectively. In this embodiment, the retaining member 16 includes four attachment tabs 26 that detachably insert into four corresponding applicator tool attachment slots 25. As shown, the tool 19 and the retaining member 18 include fluid communication openings 22 and 18, respectively. It should be understood that various combinations of tabs, slots, alignment and openings can be incorporated into the tool 19 and the member 16 without deviating from the scope of the present invention.

FIGS. 14a through 14e illustrate the steps of the claimed method of implanting an implant to an exposed surface of the cornea using the system of the present invention. The first step, shown in FIG. 14a, involves the surgical preparation of a portion of the outer surface of the cornea 38 of the eye to form a corneal flap 37, which remains attached to the cornea 38 by way of a hinge 36. This surgical step is commonly known in the art as a lamellar dissectomy, and is typically performed using a keratome (not shown). In a preferred embodiment, the flap is cut deeply enough to dissect the Bowman's membrane portion of the cornea 38. Surgically preparing a corneal flap of 100 to 200 microns, typically 160 to 180 microns, operates to eliminate tension caused by the Bowman's membrane. This step reduces the possibility of implant extrusion due to pressure generated within the cornea 38, which may be caused by the implant. As illustrated, it is preferable to leave the corneal flap 37 attached by way of a hinge 36, thereby allowing the flap 37 to be replaced in the same orientation as before the cut.

After the surface 39 is prepared, the surgeon deposits the implant 40 onto the surface 39 using the applicator 19. To retrieve the applicator tool 19, the surgeon first removes the protective seal 17 from around the bottle opening. The implant holding tool 15 is then removed from within the bottle 11 by removing the stopper 12, which holds the storage tool 15. The storage tool 15 is easily separated from the stopper 12 by holding the tool 15 about the body portion 21 and disengaging the tool 15 from the now opened slot 32. Next, the tool arm 20 can be attached to a handle 30, and the retaining member 16 removed. Removing the member 16 presents the implant 40 to the surgeon for implantation. The surgeon is able, therefore, to retrieve an implant 40 from a storage bottle 11 without having to use, at the risk of damaging or losing the implant, a grasping tool, such as tweezers or surgical forceps.

The surgeon then properly aligns the implant 40 on the applicator surface 42 by preferably passing liquid through the openings 22. At this step, the surgeon may gently guide the implant 40 to its proper alignment on the surface 42 using a cannula 35, or other similar device. The implant 40 is positioned on the applicator surface 42 by drawing off the fluid located intermediate to the implant 40 and the applicator surface 42. This can be done by placing a cotton swab, or other absorbent material, against the underside of applicator member 45, which draws off the fluid through openings 22.

Figure 14B:
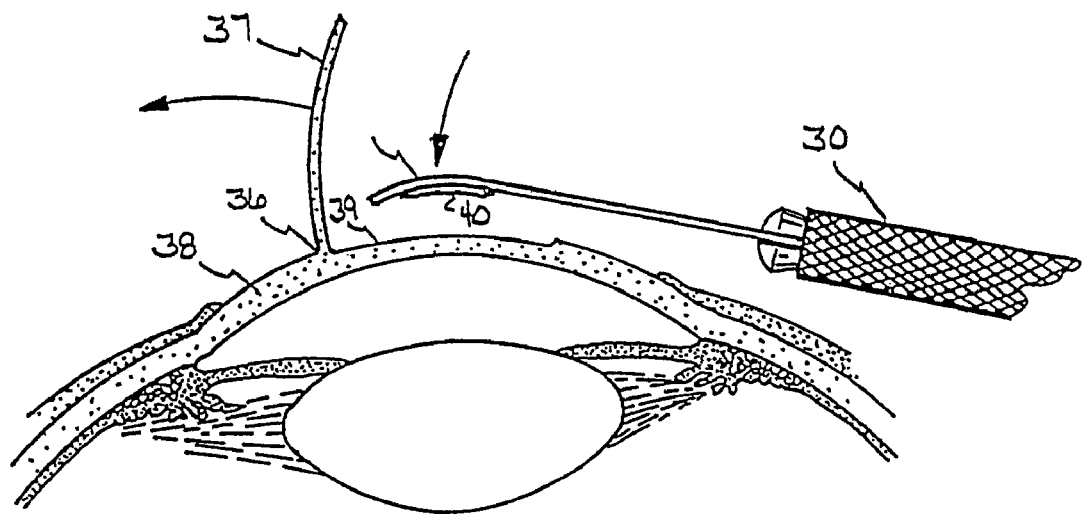
FIGS. 14a, 14b, 14c, 14d and 14e are cross-sectional views of a human eye illustrating the method of introducing an implant to the cornea surface using the implant applicator tool of the present invention.
Figure 14A:
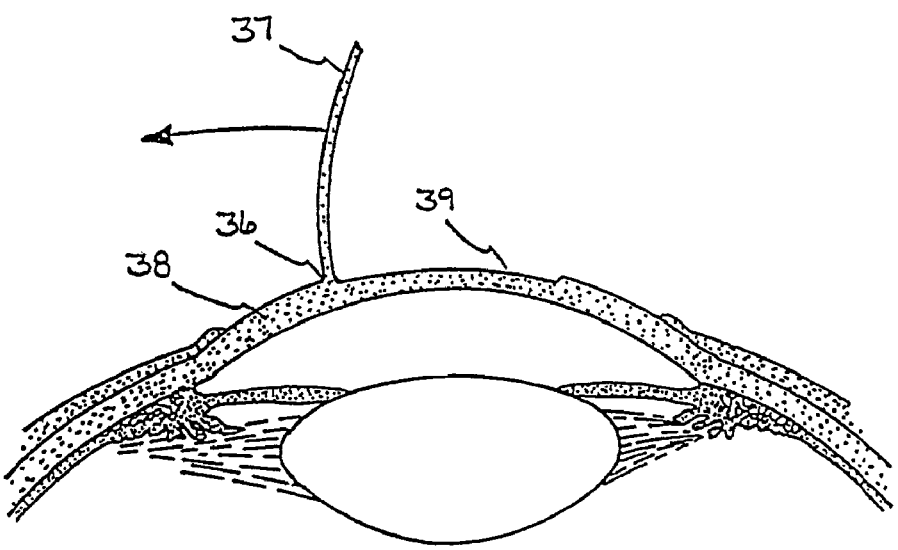

As shown in FIG. 14b, the corneal flap 37 is pulled away from the cornea implantation surface 39. The implant 40 is then positioned over the cornea implantation surface 39 by holding the applicator tool 19 in a generally horizontal position over the surface 39 with the implant 40 facing the surface 39. As shown, the applicator member 45 has an arcuate shaped applicator surface 42, which matches the curved shaped of the cornea surface 39. In this way, as illustrated in FIG. 14c, the applicator member 45 can be evenly placed over the cornea surface 39, reducing trauma to the surface 39. Specifically, the implant 40 is evenly adhered to the surface 39, reducing the need for any manipulation of the implant 40 on the surface 39, which could traumatize the eye as is described above.

Figure 14D:
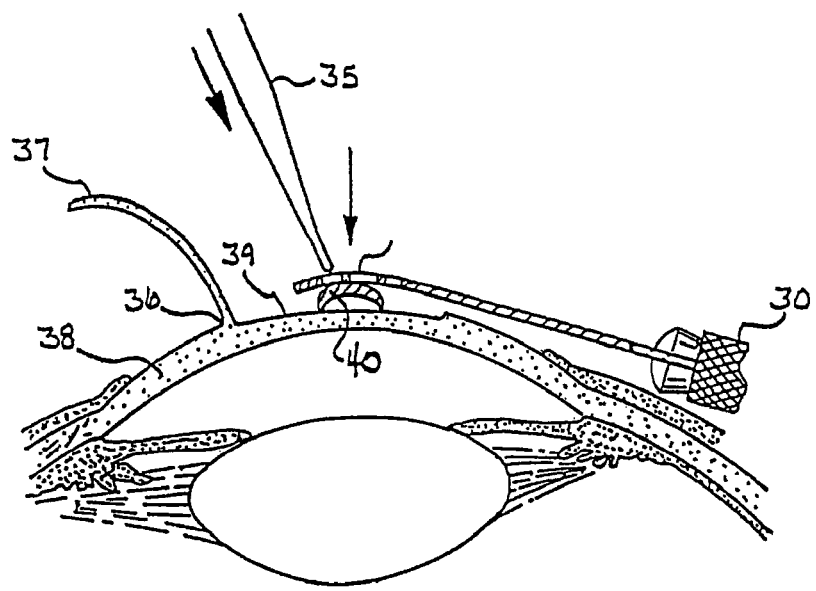
Figure 14C:
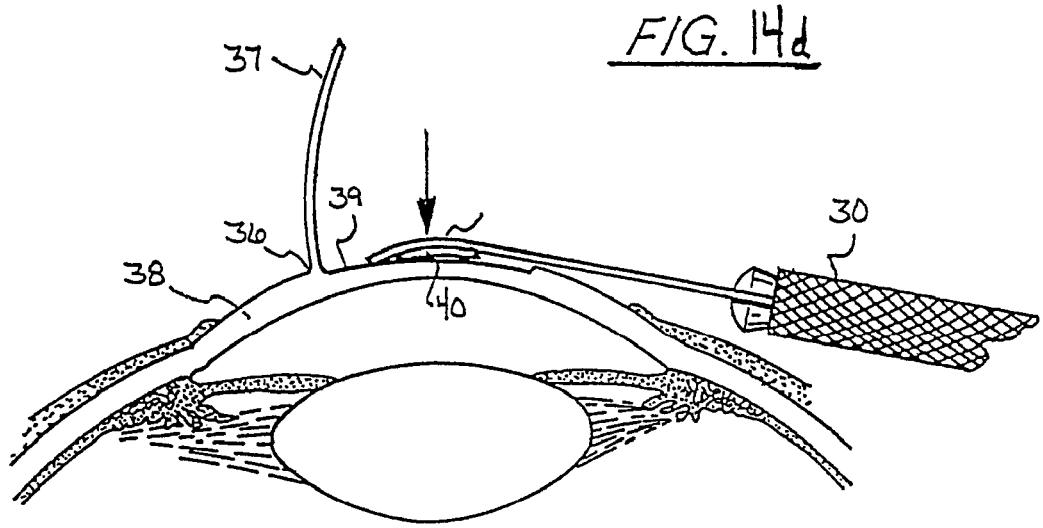
Figure 14E:
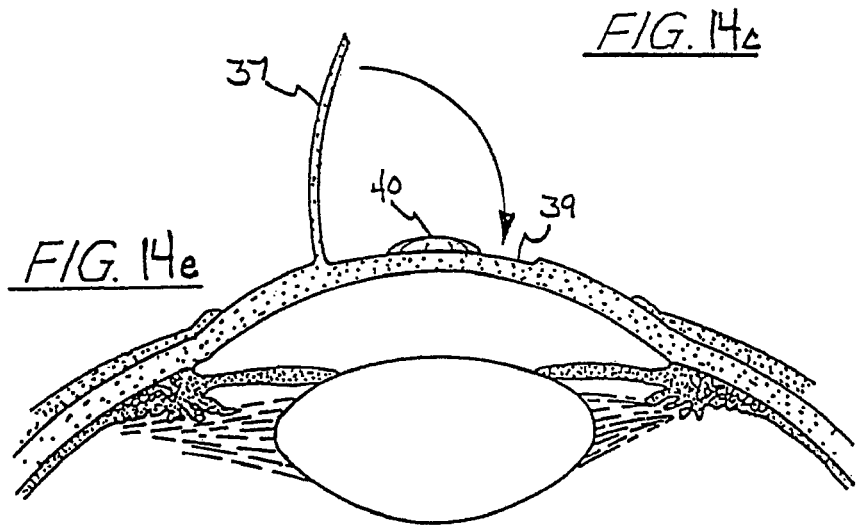

Referring to FIG. 14d, the implant 40 is deposited onto the surface 39 by gently lifting the applicator tool 19 away from the surface 39. As shown, the implant 40 remains adhered to the surface 39. The use of a cannula 35 operable to pass a volume of fluid flow through opening 22, however, can be used to ensure proper deposition of the implant 40 onto surface 39. As shown in FIG. 14e, once the implant is deposited onto the surface 39, the corneal flap 37 is replaced.

Figure 15A:
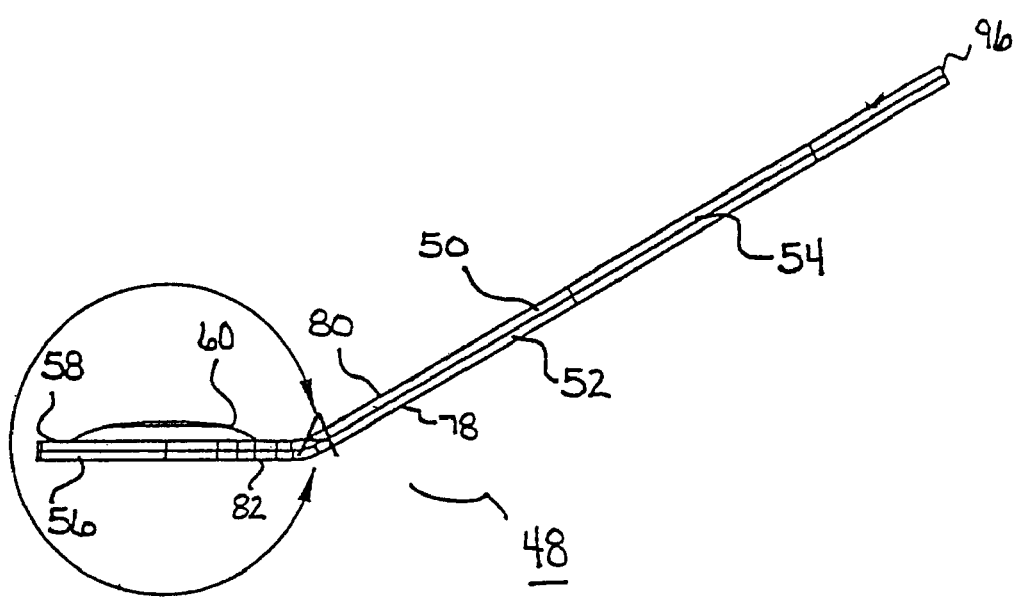
FIG. 15a is a side view of the presently preferred embodiment of implant packaging and handling system of the present invention.

As shown in FIGS. 15a through 19, there is illustrated a presently preferred embodiment for an implant packaging and handling system 48 used to apply a corneal implant to the corneal surface. Referring to FIG. 15a, the preferred embodiment includes an implant carrier member 80 having a handle portion 50 joined at an angle to a implant applicator portion 58. The system 48 further includes an implant carrier member 80, which is specially contoured to detachably connect to the implant support member 78. As illustrated, the implant support member 78 is also provided with a handle portion 52 joined at an angle to an implant support portion 56.

Figure 15B:
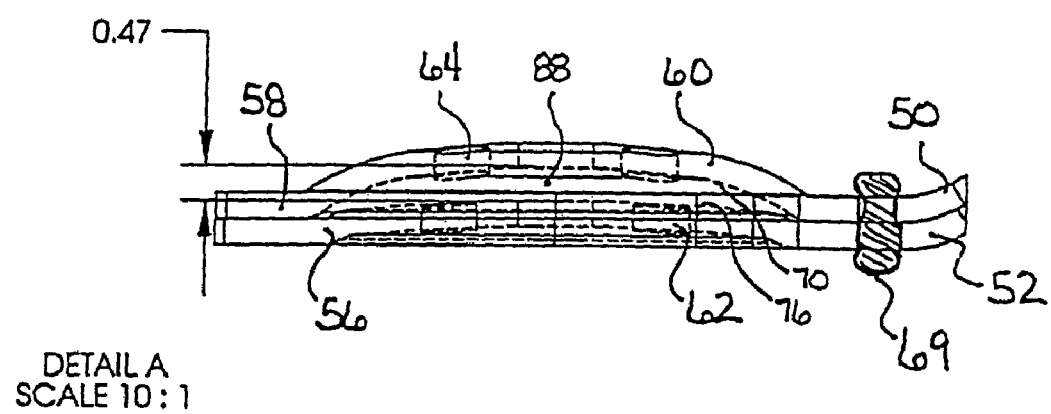
FIG. 15b is a cross-sectional view of the implant packaging and handling system shown in FIG. 15a illustrating the relation between the upper lens carrier member and the lower lens support member.

As illustrated in FIG. 15b, fastening the carrier 80 and support 78 members together operably aligns the implant applicator portion 58 and implant support portion 56. In this embodiment, the handle portions 50 and 52 are adjacently positioned so as to form a support handle 54 having an end 96 that is held within by an opening 32 in a vial stopper 12 during storage conditions, as illustrated by FIG. 1. In this way, the concave surface 70 of the applicator portion 58 overlaps the upper implant support surface 76, which is preferably a convex surface, of the support portion 56. This overlapping arrangement forms a chamber 88 between the two surfaces, 70 and 76, which provides a storage space to hold an implant therein.

Figure 16A:
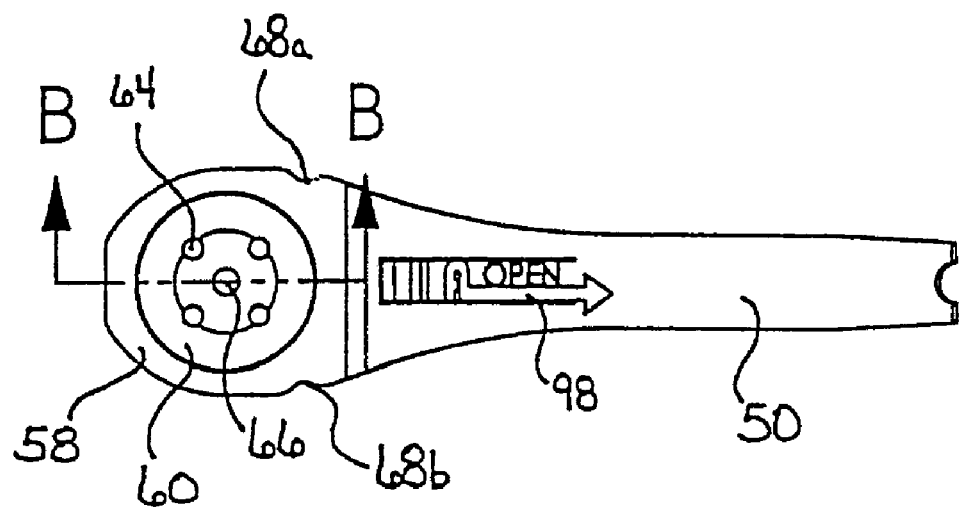
FIG. 16a is a top view of the upper lens carrier member of the implant packaging and handling system of the present invention.
Figure 16B:
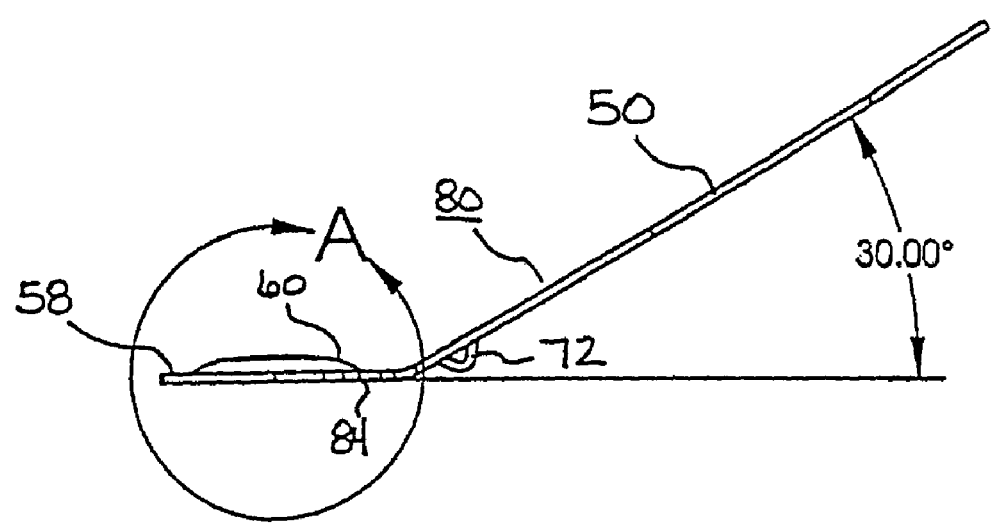
FIG. 16b is a side view of the upper lens carrier member of the implant packaging and handling system of the present invention.
Figure 16C:
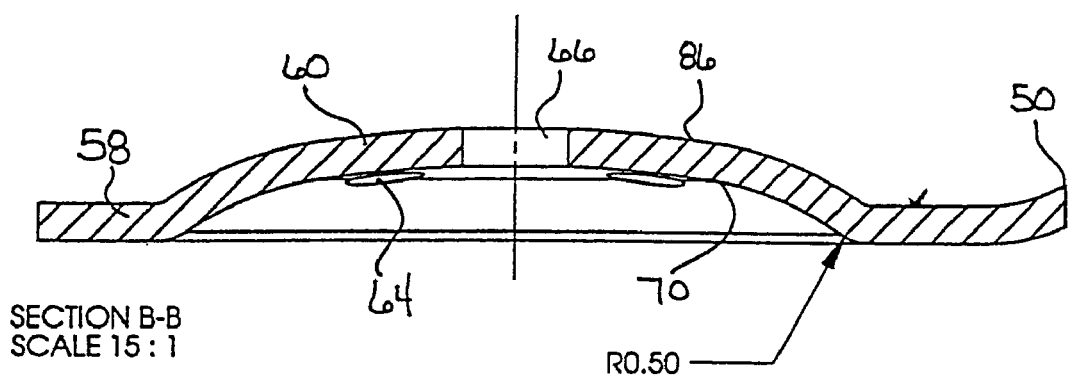

Referring to FIG. 16c, which is shown a cross-sectional view of the preferred implant applicator portion 58. The applicator portion 58 includes a recessed or domed portion having an upper surface 86 and lower surface 70. The lower surface 70 is specially contoured to have a radius of curvature that is greater than the radius of curvature of an implant that is being packaged. Such design is advantageous in assisting with the release of the lens implant from the applicator surface 70. More particularly, a corneal implant generally includes a posterior surface that is applied directly to the corneal surface and an anterior surface that is covered by a corneal flap following the application of the implant to the corneal surface. Similar to the method described in detail above, applying the implant to the corneal surface is achieved by setting the applicator surface 70 of the applicator portion 58 in contact with the corneal surface and then lifting the applicator portion 58 away from the corneal surface, wherein the anterior surface of the implant remains adhered to the corneal surface and the posterior surface of the implant releases from the applicator surface 70. To both enhance deposition of the implant onto the corneal surface and prevent the implant from remaining adhered to the applicator lower surface 70, the applicator lower surface 70 is provided with a radius of curvature that is greater than the curvature of the anterior surface of the particular implant that is packaged and held in the chamber 88 between the implant applicator portion 58 and the support portion 56. In this way, the anterior surface of the implant and the applicator lower surface 70 are not complementary, and, thus, are more easily separated.

In another embodiment, the applicator surface 70 is provided with an indented ring or recessed applicator surface (as is shown in FIG. 12 and indicated by numeral 29). The recessed surface is preferably circular, thereby allowing a substantially circular implant to be centrally positioned on the applicator surface 70.

To further enhance displacement of the implant from the applicator surface 70, a plurality of openings 64 are provided through the applicator surface 70 through which a volume of fluid can be passed or withdrawn away from the implant resting against the applicator surface 70. Particularly, the openings 64 provide a fluid passage for drawing fluid away from the implant using a cotton swab, or other absorbent material, placed against the upper surface 86 of the applicator portion 58. Additionally, a central opening 66 is provided on the applicator surface to assist with the proper alignment of the implant and the deposition of the implant onto the cornea surface. Specifically, a cannula or like instrument can be inserted through the central opening 66 to depress and assist the release of the implant from the applicator surface 76, as is described in greater detail above. As is also described above, the central opening 66 defines a circular opening having a diameter greater than the diameter of the surrounding openings 64. In this way, the user is provided with a central point of reference, which enables the user to align the applicator surface 70 with the optical axis of the eye, and, thus, properly position the implant.

Figure 17A:
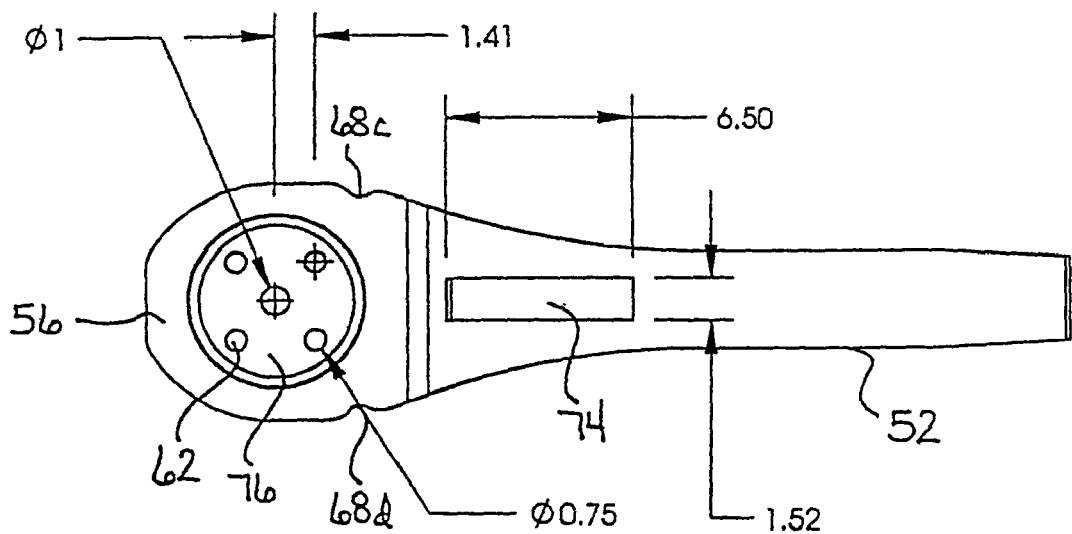
FIG. 17a is a top view of the lower lens support member of the implant packaging and handling system of the present invention.
Figure 17B:
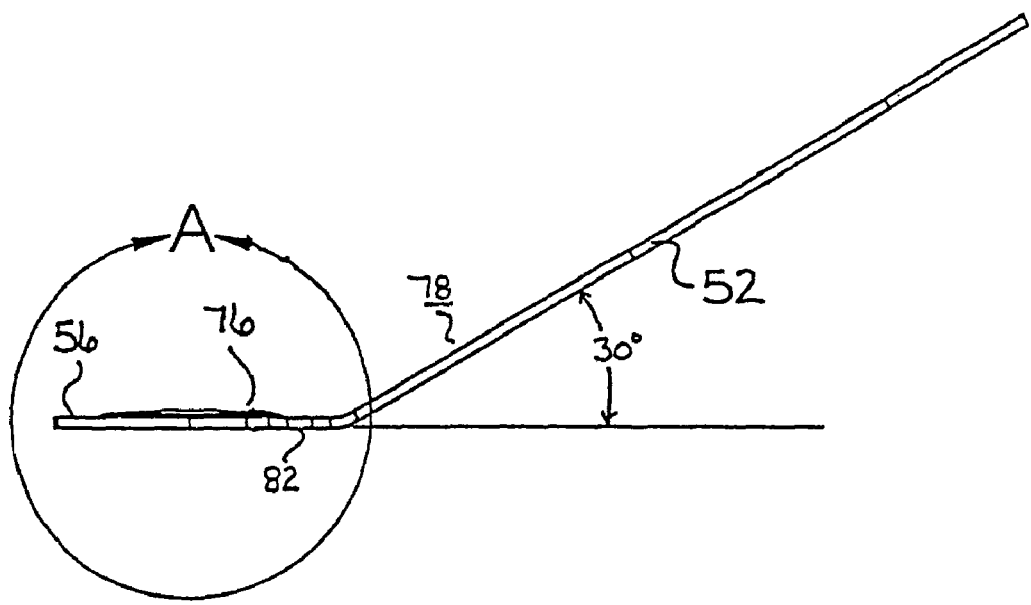
FIG. 17b is a side view of the lower lens support member of the implant packaging and handling system of the present invention.
Figure 17C:
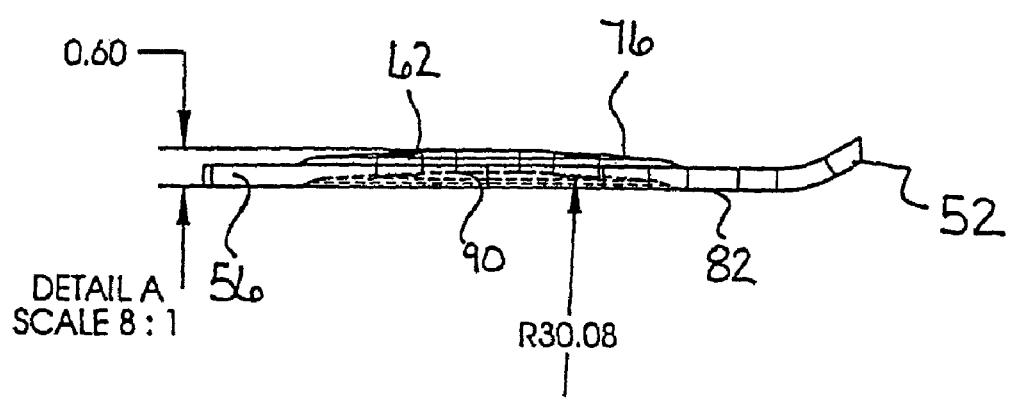
FIG. 17c is a cross-sectional view of the lower lens support member shown in FIGS. 17a and 17b.

Referring to FIGS. 17*a* through 17*c*, there is shown the implant support member 78. As illustrated, the implant support member 78 has a handle portion 52 joined to an implant support portion 56. The implant support portion 56 comprises a platform portion 82 disposed about an upper implant support surface 76 having an opposing lower surface 90 that is recessed relative to the lower surface of the platform portion 82. The support 76 and lower 90 surfaces define a plurality of openings therethrough to facilitate the passage of liquid to and away from the implant.

Referring to FIG. 16*b* the support portion 56 is shown as being angularly connected to the handle portion 52. In the present embodiment, it is advantageous to provide an angle between the handle portion 52 and the lower surface of the platform portion 52 of between about 30° and about 60°. Likewise, and as illustrated in FIG. 17*b*, the angular connection between the applicator portion 58 and handle portion 50 forms is generally between about 30° and about 60° relative to the lower surface of platform portion 84. A preferable angular connection between the handle portions 50 and 52 and platform portions 84 and 82, respectively, is about 45°. Though preferred angles are provided, it is to be understood that a range of angular connections can be used without deviating from the scope of the present invention.

Referring to FIGS. 15*b*, 16*a* and 17*a*, there is illustrated a preferred embodiment to maintain the implant support member 78 detachably connected to the implant carrier member 80. Specifically, as illustrated by FIG. 16*a*, the carrier member 80 is provided with a pair of notches or grooves, 68*a* and 68*b*, along opposite edges of the carrier member 80. More particularly, the notches or grooves, 68*a* and 68*b*, are located on opposite sides of the implant applicator portion 58. Likewise, the support member 78 is provided with a pair of notches or grooves, 68*c* and 68*d*, located on opposite sides of the implant support portion 56 of the support member 78. In this way, the carrier member 80 can be securely fastened to the support member 78 by aligning notch 68*a* with 68*c*, and 68*b* with 68*d*, and then positioning a fastening means about the two members and securely within the matched notches. Referring to FIG. 15*b*, a fastening means can include an elastic band 69, which is placed about each member, 78 and 80, and secured within each of the respective notches (68*a-d*) to secure the members together in a detachable manner. Alternatively, metal or plastic clips could be used to fasten together the two members, 78 and 80. It should be understood, however, that various ways can be utilized to fasten the two members together in a detachable manner without deviating from the scope of the present invention.

Referring to FIG. 17*a*, a preferred embodiment of the present invention comprises a space or slot 74 through the handle portion 52 of the support member 78 for receiving and interlocking with a tab portion 72. As shown in FIG. 16*b*, there is illustrated a tongue or tab portion 72 extending from the lower surface of the handle portion 50 of the carrier member 80. In use, the carrier member 80 is positioned in overlapping relation to the support member 78 such that the tap portion 72 is inserted into the slot 74. Once inserted, the tab portion 72 holds the carrier member 80 together with the support member 78. To provide further attachment, the band 69 is then place about the implant applicator portion 58 and implant support portion 56, as is described in more detail above. In its preferred use, the user initially removes the band 69 or other attachment means from about the adjacently fastened members, 78 and 80. Once removed, the user simply slides the handle portion 50 in the direction indicated by the arrow 98 or other similar indicia. In this way, the tab 72 is slidably disengages from the slot 74 and the two members, 78 and 80, are separated. Once separated, the top carrier member 80 is used to apply the implant to the cornea surface. The handle portion 50 of the carrier member 80 can be attached to a surgical-style handle 30 as illustrated in FIGS. 9 and 10. The user is then able to easily manipulate the carrier member 80 for depositing the implant onto the cornea surface.

Because of the special design of the support surface 76, the lens implant will preferably remain adhered to the carrier applicator surface 70 on the carrier member 80 upon separation of the two members, 78 and 80. More particularly, a preferred embodiment for the support surface 76 comprises fabricating the surface 76 to have a more uneven or rough contour than the adjacent applicator surface 70. Specifically, the applicator surface 70 is provided as a smooth or polished surface, while the support surface 76 is provided as a more rough or uneven surface 76. In this embodiment, it is not critical that the surface 70 be microscopically smooth, though it is preferred; however, it is critical that the surface 70 be more smooth than the corresponding support surface 76. In this manner, the applicator surface 70 provides a smoother surface area for directly contacting and adhering to the lens implant. The support surface 76, however, is preferably fabricated so as to have a contour characterized by minute bumps or rounded portions along the surface 76. This contoured surface can be fabricated by manufacturing the support surface 76 from polypropylene comprising polytetrafluoroethylene beads embedded in the polypropylene surface. Polytetrafluoroethylene is sold under the trade name TEFLON. In this embodiment, the beads maintain their general conformation when embedded, which results in the surface 76 having raised bumps, rounded portions, or the like. Alternatively, the support surface 76 can be roughened, etched, notched, scored or made to be imperfect using any one of molding, stamping or other mechanical techniques generally known in the art. In this way, the surface 76 is less able to adhere to the surface of the implant than is the more smooth applicator surface 70, and the implant will preferentially remain adhered to the applicator surface 70 upon separation of the two members, 78 and 80.

As described above, the implant can be further directed to maintain an adhering position on the applicator surface 70 by removing the system 48 from the storage bottle 11 and turning the system 48 such that the carrier member 80 is facing downwards. Next, the user simply places an absorbent material against the top surface 60 of the applicator portion 58 so as to draw fluid from within the chamber 88 through the openings 64. This results in the implant being lowered to a resting position against the applicator surface 70 as the storage fluid is withdrawn from the chamber 88.

In another presently preferred embodiment, one or more of the various members of the system 48 is made from a polymer or plastic material. For instance, the system 48 components could be made from one or a combination of the following polymers: Polytetrafluoroethylene (sold under the trade name TEFLON), Polypropylene, or Polysulfone (sold under the trade name UDEL). Alternatively, portions of each component member could be made from a polymer or plastic together with a portion comprising stainless steel or other metal or semi-metal material. For instance, the handle portion 50 of the implant carrier member 80 could be manufactured from stainless steel, and the applicator portion 58 could be manufactured from a polymer material. The handle and applicator portions could then be welded or interlocked together using various fabrication techniques known in the art. It should also be understood that various other polymers or polymer combinations can be utilized without deviating from the scope of the present invention.

As described above, the present system 48 is used to maintain an implant in a hydrated condition during storage and shipping. More particularly, and as is shown in FIG. 15a, the handle portions 50 and 52 of each member when positioned together form a support handle 54 adapted to insert into a vial stopper. As described above, and illustrated in FIGS. 5 through 8, a means for holding the system 48 in a storage vial comprises inserting the end 96 of the support handle 54 into an opening 32 provided in a stopper 12. Once inserted into the opening 32, the stopper 12 is placed in the vial opening thereby positioning the implant within the vial and in contact with a volume of storage fluid in the vial. It should be understood that the presently described system 48 for holding and applying the implant to the corneal surface is readily adapted for use with the storage vial and stopper described in more detail above. In this way, the implant is contained within the chamber 88 and maintained in a hydrated condition by the passage of fluid through the respective openings 62, 64 and 66.

Figure 18:
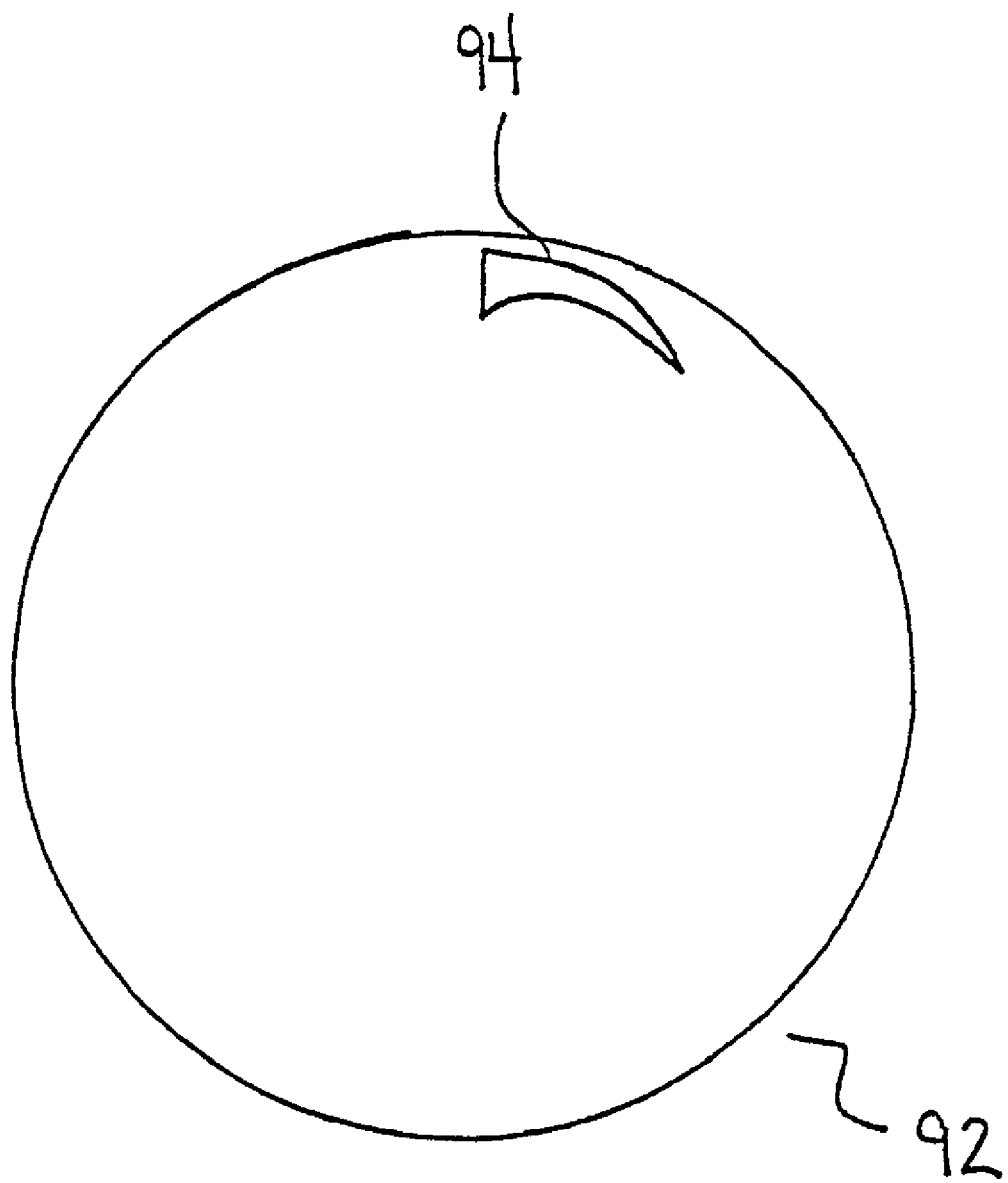
FIG. 18 is a top view of a lens implant of the present invention showing an asymmetrical mark for proper orientation of the lens on the cornea surface.
Figure 19:
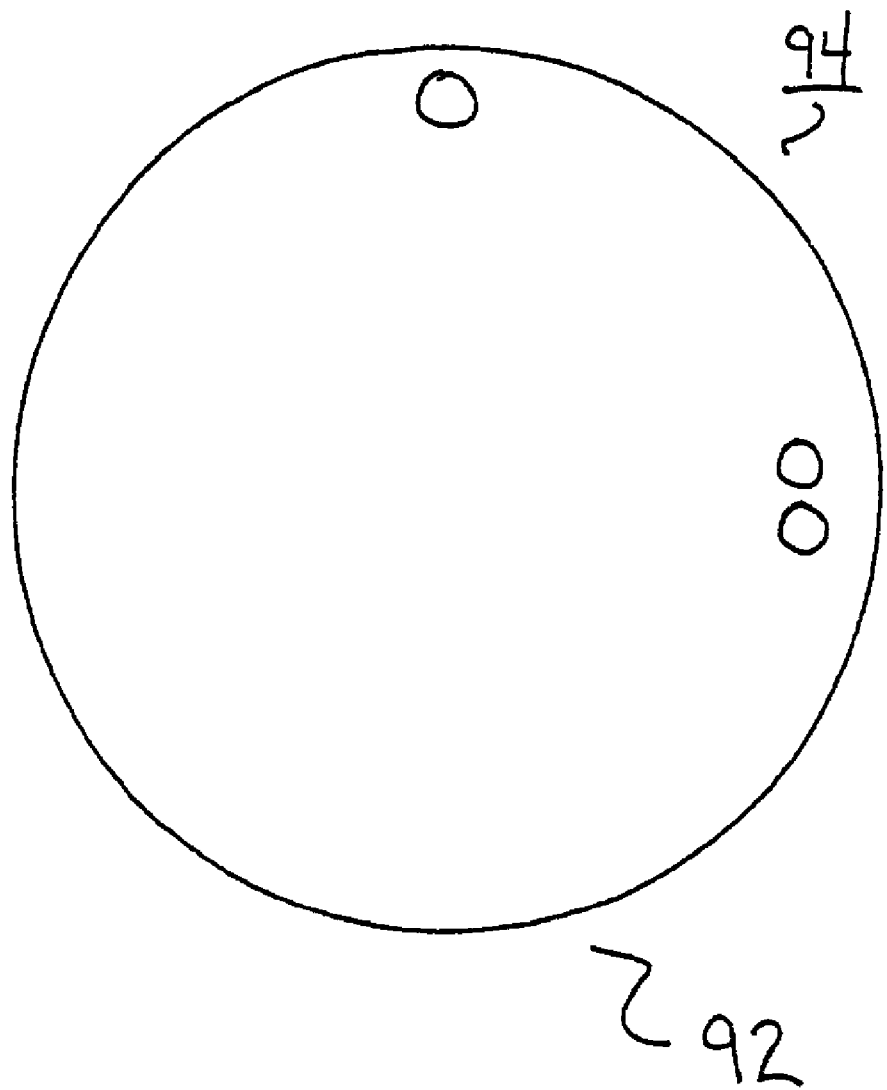
FIG. 19 is a top view of a lens implant of the present invention showing asymmetrical markings for proper orientation of the lens on the cornea surface.
Figure 20:
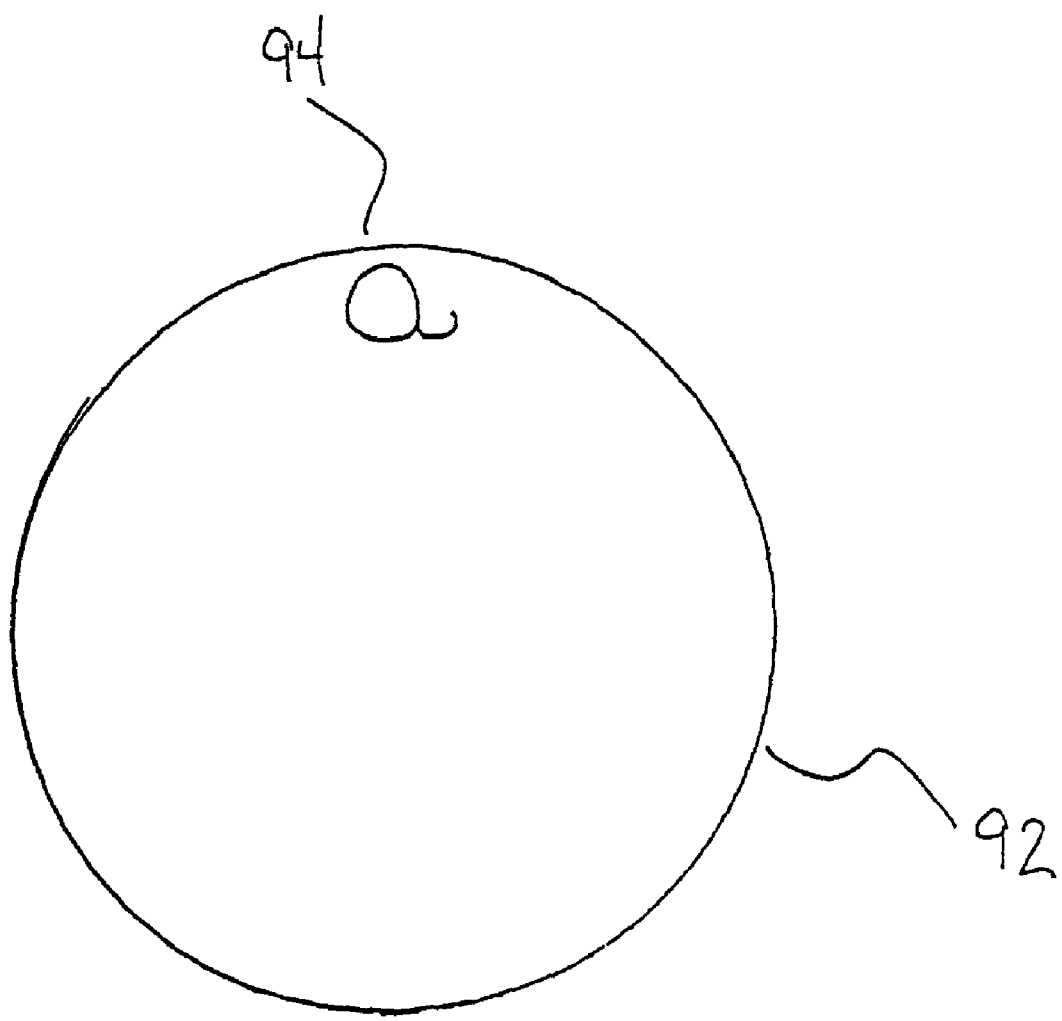
FIG. 20 is a top view of a lens implant of the present invention showing the posterior surface of the lens implant having the letter "a" imprinted on the anterior surface.

In the present embodiment, the lens implant 92 is packaged within the chamber 88 defined by the applicator surface 70 and carrier support surface 76. It is to be understood that the height of this space is designed to be sufficiently narrow that the implant 92 remains properly oriented within the chamber 88 during storage and handling conditions. In this way, the user simply detaches the upper implant member 80 from the implant support member 78 and deposits the implant to the corneal surface by placing the applicator surface 70, on which the implant is adhered to, directly to the corneal surface. To ensure that the implant is properly oriented, however, the implant is provided with special asymmetric markings, which the user views to make a determination that the implant is resting against the corneal surface in a proper orientation. Referring to FIGS. 18-20, there are shown three exemplary embodiments of asymmetric markings 94 that can be utilized to properly orient the lens implant. As shown by FIGS. 18 and 19, the markings are preferably positioned in a clockwise orientation. In another embodiment, shown in FIG. 20, a letter can be placed on the posterior surface of the implant. In this way, if the implant's posterior surface is placed onto the cornea surface, then the letter will not read properly. For instance, FIG. 20 shows the letter "a" on the posterior surface of the implant 92. If the implant 92 is not positioned right side up on the cornea surface, then the letter will read backwards. In this embodiment, any letter can be used so long as it has an asymmetric design. For instance, "R", "P", "C", etc. It is to be understood, however, that other symmetrical or asymmetric markings and orientations can be used without deviating from the scope of the present invention.

In this embodiment, the markings 94 can be positioned onto the lens using laser engraving, and/or printing with ink. Alternatively, openings through the lens can be asymmetrically positioned about the lens. It is important, however, that the markings 94 be positioned as far from the optical zone as possible to prevent optical distortion. It is to be further understood that various methods and techniques for placing the mark on the lens can be used without deviating from the scope of the present invention. For instance, notches could be positioned in an asymmetric orientation about the edge of the lens implant.

In another embodiment, the system 48 is provided as a component of a kit used to store, handle and implant the implant onto the cornea surface. Specifically, the system 48 is provided within a storage bottle (as illustrated above in FIG. 1) having a volume of storage fluid contained therein. In this way, the handle end 96 is inserted into the opening 32 (FIG. 5) in the stopper, and the stopper is placed into the bottle 11, which positions the implant holding chamber 88 located opposite the handle end 96 within the bottle. In this way, the implant 92 is positioned in communication with the storage fluid. The implant 92 is provided having the markings 94 shown in FIGS. 18 and 19 to assist the user with properly orienting and/or to ensure that the implant is positioned right side up on the cornea surface.

Various embodiments of the of the present invention have been described herein. It should be understood by those of ordinary skill in the art, however, that the above described embodiments of the present invention are set forth merely by way of example and should not be interpreted as limiting the scope of the present invention, which is defined by the appended claims. Many other alternative embodiments, variations and modifications of the foregoing embodiments that embrace various aspects of the present invention will also be understood upon a reading of the detailed description in light of the prior art. For instance, it will be understood that features of one embodiment may be combined with features of other embodiments while many other features may be omitted (or replaced) as being nonessential to the practice of the present invention.

The invention claimed is:

1. A packaging and handling system, comprising:
   a storage container having a fluid contained in said container; and
   an implant applicator tool for implanting a corneal implant contained in said container, said applicator tool comprising:
   an applicator first end, and an applicator second end,
   said applicator second end having a concave surface contoured to hold an implant for application of the implant to the eye; and a retaining member, said retaining member adapted to detachably engage to said applicator second end surface so as to define an enclosure to retain an implant, wherein said applicator second end has a recessed surface adapted to hold the implant in a planar position.

2. The system claimed in claim 1, further including a handle for detachably connecting to said implant applicator tool.

3. The system claimed in claim 1, wherein said applicator second end has a portion of a surface that is arcuate shaped.

4. The system claimed in claim 1, wherein said recessed surface defines a circular recess.

5. The system claimed in claim 4, wherein said circular recess has a circumference at least as great as the circumference of a circular implant.

6. The system claimed in claim 1, wherein said retaining member has one or more engagement tabs projecting from said retaining member, said applicator tool having tab engagement slots correspondingly aligned to receive said retaining member engagement tabs.

7. The system claimed in claim 1, wherein said applicator second end includes a centrally positioned alignment opening.

8. The system claimed in claim 1 or claim 7, wherein said applicator second end includes an applicator alignment notch.

9. The system claimed in claimed 1, wherein the applicator second end has a portion of a surface having a plurality of openings therethrough.

10. A packaging and handling system, comprising:
    a storage container having a fluid contained in said container; and
    an implant applicator tool contained in said container, said applicator tool comprising:
        an applicator first end adapted to detachably connect to a handle;
        an applicator second end having a concave surface containing a circular recess to hold an implant for application of the implant to the eye; and
        at least a portion of said surface having a plurality of openings therethrough.

11. The system claimed in claim 10, further including a handle for detachably connecting to said implant applicator tool.

12. The system claimed in claim 10, wherein at least a portion of said applicator surface is arcuate shaped.

13. The system claimed in claim 10, wherein said circular recess has a circumference at least as great as the circumference of a circular implant.

14. The system claimed in claim 10, further including a retaining member, said retaining member adapted to detachably engage said implant applicator tool so as to define an enclosure to retain an implant.

15. The system claimed in claim 14, wherein said retaining member has one or more engagement tabs projecting from said retaining member, said applicator tool having tab engagement slots correspondingly aligned to receive said retaining member engagement tabs.

16. The system claimed in claim 10, wherein said applicator second end includes a centrally positioned alignment opening.

17. The applicator system claimed in claim 10 wherein said recess is adapted to hold the implant in a substantially planar position.

* * * * *